(12) United States Patent
Azure et al.

(10) Patent No.: US 9,526,911 B1
(45) Date of Patent: Dec. 27, 2016

(54) IMMUNE MEDIATED CANCER CELL DESTRUCTION, SYSTEMS AND METHODS

(75) Inventors: Larry Azure, La Conner, WA (US);
Charles E. Hill, Issaquah, WA (US);
Andrew L. Azure, Mount Vernon, WA (US); Rafael Ponce, Seattle, WA (US);
Lawrence L. Kunz, Greenbank, WA (US)

(73) Assignee: LAZURE SCIENTIFIC, INC., Issaquah, WA (US)

( * ) Notice: Subject to any disclaimer, the term of this patent is extended or adjusted under 35 U.S.C. 154(b) by 1324 days.

(21) Appl. No.: 13/095,804

(22) Filed: Apr. 27, 2011

Related U.S. Application Data

(60) Provisional application No. 61/328,580, filed on Apr. 27, 2010.

(51) Int. Cl.
| | |
|---|---|
| *A61N 1/00* | (2006.01) |
| *A61N 5/02* | (2006.01) |
| *A61N 1/40* | (2006.01) |
| *A61N 5/06* | (2006.01) |
| *A61B 18/14* | (2006.01) |
| *A61B 18/18* | (2006.01) |
| *A61B 17/00* | (2006.01) |
| *A61B 18/00* | (2006.01) |

(52) U.S. Cl.
CPC ............... *A61N 1/403* (2013.01); *A61N 5/025* (2013.01); *A61N 5/0625* (2013.01); *A61B 18/14* (2013.01); *A61B 18/1477* (2013.01); *A61B 18/18* (2013.01); *A61B 2017/00867* (2013.01); *A61B 2018/0016* (2013.01); *A61B 2018/143* (2013.01); *A61B 2018/1425* (2013.01); *A61B 2018/1432* (2013.01); *A61B 2018/1475* (2013.01)

(58) Field of Classification Search
CPC ............... A61B 18/18; A61B 18/1815; A61B 2018/1861; A61B 2018/1869; A61N 5/045
USPC ....................... 607/101; 606/34, 41
See application file for complete search history.

(56) References Cited

U.S. PATENT DOCUMENTS

| | | |
|---|---|---|
| 3,991,770 A | 11/1976 | LeVeen |
| 4,016,886 A | 4/1977 | Doss et al. |
| 4,346,715 A | 8/1982 | Gammell |
| 4,448,198 A | 5/1984 | Turner |
| 4,676,258 A | 6/1987 | Inokuchi et al. |
| 4,732,161 A | 3/1988 | Azam et al. |
| 4,763,671 A | 8/1988 | Goffinet |
| 4,821,725 A | 4/1989 | Azam et al. |
| 4,860,752 A | 8/1989 | Turner |
| 5,277,201 A | 1/1994 | Stern |
| 5,370,677 A | 12/1994 | Rudie et al. |
| 5,472,441 A | 12/1995 | Edwards et al. |
| 5,630,426 A | 5/1997 | Eggers et al. |
| 5,681,282 A | 10/1997 | Eggers et al. |
| 5,807,395 A | 9/1998 | Mulier et al. |

(Continued)

OTHER PUBLICATIONS

Aoyagi et al., "Effects of Moderate Hyperthermia on the Rabbit Sacroma Model," *Neurol. Med. Chir. (Tokyo)* 43:105-111 (2003).

(Continued)

*Primary Examiner* — Kaitlyn Smith
(74) *Attorney, Agent, or Firm* — Wilson Sonsini Goodrich & Rosati

(57) ABSTRACT

Systems and methods for delivering electric fields to a target tissue of a patient for destruction of cancerous cells so as to elicit or induce a specific anti-cancerous cell immune response in the patient.

17 Claims, 9 Drawing Sheets

(56) References Cited

U.S. PATENT DOCUMENTS

| | | | |
|---|---|---|---|
| 5,810,804 A | 9/1998 | Gough et al. | |
| 5,827,276 A | 10/1998 | LeVeen et al. | |
| 5,855,576 A | 1/1999 | Leveen et al. | |
| 5,868,740 A | 2/1999 | LeVeen et al. | |
| 5,935,123 A | 8/1999 | Edwards et al. | |
| 5,957,922 A | 9/1999 | Imran | |
| 5,968,041 A | 10/1999 | Edwards | |
| 6,050,992 A | 4/2000 | Nichols | |
| 6,071,280 A | 6/2000 | Edwards et al. | |
| 6,090,105 A | 7/2000 | Zepeda et al. | |
| 6,107,540 A * | 8/2000 | Sawyer et al. | 800/10 |
| 6,136,020 A | 10/2000 | Faour | |
| 6,148,236 A | 11/2000 | Dann | |
| 6,149,620 A | 11/2000 | Baker et al. | |
| 6,177,410 B1 * | 1/2001 | Holt et al. | 514/44 R |
| 6,212,433 B1 | 4/2001 | Behl | |
| 6,231,570 B1 | 5/2001 | Tu et al. | |
| 6,246,912 B1 | 6/2001 | Sluijter et al. | |
| 6,365,797 B1 * | 4/2002 | Sawyers et al. | 800/9 |
| 6,402,742 B1 | 6/2002 | Blewett et al. | |
| 6,419,653 B2 | 7/2002 | Edwards et al. | |
| 6,440,127 B2 | 8/2002 | McGovern et al. | |
| 6,461,296 B1 * | 10/2002 | Desai | 600/210 |
| 6,477,426 B1 | 11/2002 | Fenn et al. | |
| 6,517,534 B1 | 2/2003 | McGovern et al. | |
| 6,537,272 B2 | 3/2003 | Christopherson et al. | |
| 6,682,555 B2 | 1/2004 | Cioanta et al. | |
| 6,738,663 B2 | 5/2004 | Schroeppel et al. | |
| 6,743,226 B2 | 6/2004 | Cosman et al. | |
| 6,797,692 B1 * | 9/2004 | Ikonomidou | 424/85.2 |
| 6,850,804 B2 | 2/2005 | Eggers et al. | |
| 6,853,864 B2 | 2/2005 | Litovitz | |
| 6,866,624 B2 | 3/2005 | Chornenky et al. | |
| 6,868,289 B2 | 3/2005 | Palti | |
| 6,939,324 B2 * | 9/2005 | Gonnelli et al. | 604/142 |
| 6,939,346 B2 | 9/2005 | Kannenberg et al. | |
| 6,944,504 B1 | 9/2005 | Arndt et al. | |
| 6,958,064 B2 | 10/2005 | Rioux et al. | |
| 6,962,587 B2 | 11/2005 | Johnson et al. | |
| 6,993,394 B2 | 1/2006 | Eggers et al. | |
| 6,994,706 B2 | 2/2006 | Chornenky et al. | |
| 7,016,725 B2 | 3/2006 | Palti | |
| 7,053,063 B2 | 5/2006 | Rubinsky et al. | |
| 7,089,054 B2 | 8/2006 | Palti | |
| 7,135,029 B2 | 11/2006 | Makin et al. | |
| 7,136,699 B2 | 11/2006 | Palti | |
| 7,146,210 B2 | 12/2006 | Palti | |
| 7,238,182 B2 | 7/2007 | Swoyer et al. | |
| 7,311,708 B2 | 12/2007 | McClurken | |
| 7,333,852 B2 | 2/2008 | Palti | |
| 7,395,112 B2 * | 7/2008 | Keisari et al. | 607/3 |
| 7,722,606 B2 | 5/2010 | Azure | |
| 8,788,037 B2 * | 7/2014 | Della Rocca et al. | 607/3 |
| 2002/0058933 A1 | 5/2002 | Christopherson et al. | |
| 2002/0077627 A1 | 6/2002 | Johnson et al. | |
| 2002/0077676 A1 | 6/2002 | Schroeppel et al. | |
| 2002/0082610 A1 | 6/2002 | Cioanta et al. | |
| 2002/0083478 A1 * | 6/2002 | Sawyers et al. | 800/10 |
| 2002/0198567 A1 * | 12/2002 | Keisari et al. | 607/3 |
| 2003/0073908 A1 * | 4/2003 | Desai | 600/464 |
| 2003/0100814 A1 * | 5/2003 | Kindlein | 600/4 |
| 2003/0125615 A1 * | 7/2003 | Schwartz | 600/374 |
| 2003/0130575 A1 | 7/2003 | Desai | |
| 2003/0139788 A1 * | 7/2003 | Eggers et al. | 607/96 |
| 2003/0150372 A1 | 8/2003 | Palti | |
| 2003/0194403 A1 * | 10/2003 | van de Winkel et al. | 424/145.1 |
| 2004/0068169 A1 * | 4/2004 | Mansfield et al. | 600/407 |
| 2004/0068297 A1 | 4/2004 | Palti | |
| 2004/0087939 A1 | 5/2004 | Eggers et al. | |
| 2004/0106904 A1 * | 6/2004 | Gonnelli et al. | 604/173 |
| 2004/0116952 A1 | 6/2004 | Sakurai et al. | |
| 2004/0158288 A1 * | 8/2004 | Keisari et al. | 607/1 |
| 2004/0176804 A1 | 9/2004 | Palti | |
| 2004/0230190 A1 | 11/2004 | Dahla et al. | |
| 2005/0013875 A1 * | 1/2005 | Kobayashi et al. | 424/647 |
| 2005/0090711 A1 * | 4/2005 | Fuchs et al. | 600/113 |
| 2005/0090732 A1 * | 4/2005 | Ivkov | A61N 1/406 600/411 |
| 2005/0171523 A1 | 8/2005 | Rubinsky et al. | |
| 2005/0171574 A1 | 8/2005 | Rubinsky et al. | |
| 2005/0209640 A1 | 9/2005 | Palti | |
| 2005/0209641 A1 | 9/2005 | Palti | |
| 2005/0209642 A1 | 9/2005 | Palti | |
| 2005/0222646 A1 | 10/2005 | Kroll et al. | |
| 2005/0234439 A1 | 10/2005 | Underwood | |
| 2005/0240173 A1 | 10/2005 | Palti | |
| 2005/0240228 A1 | 10/2005 | Palti | |
| 2005/0251126 A1 | 11/2005 | Gellman et al. | |
| 2006/0079883 A1 | 4/2006 | Elmouelhi et al. | |
| 2006/0079947 A1 * | 4/2006 | Tankovich | A61N 5/0616 607/89 |
| 2006/0149226 A1 | 7/2006 | McCullagh et al. | |
| 2006/0149341 A1 | 7/2006 | Palti | |
| 2006/0155270 A1 | 7/2006 | Hancock et al. | |
| 2006/0167499 A1 | 7/2006 | Palti | |
| 2006/0217694 A1 | 9/2006 | Chin et al. | |
| 2006/0217703 A1 | 9/2006 | Chornenky et al. | |
| 2006/0233867 A1 | 10/2006 | Palti | |
| 2006/0237019 A1 | 10/2006 | Palti | |
| 2006/0241547 A1 | 10/2006 | Palti | |
| 2006/0241577 A1 | 10/2006 | Balbierz et al. | |
| 2006/0264752 A1 | 11/2006 | Rubinsky et al. | |
| 2006/0282122 A1 | 12/2006 | Palti | |
| 2007/0043345 A1 | 2/2007 | Davalos et al. | |
| 2007/0135879 A1 | 6/2007 | McIntyre et al. | |
| 2007/0225766 A1 | 9/2007 | Palti | |
| 2008/0033422 A1 | 2/2008 | Turner et al. | |
| 2008/0071262 A1 * | 3/2008 | Azure | 606/34 |
| 2008/0071264 A1 * | 3/2008 | Azure | 606/41 |
| 2008/0071265 A1 * | 3/2008 | Azure | 606/41 |
| 2008/0132963 A1 * | 6/2008 | Keisari et al. | 607/3 |
| 2008/0167555 A1 * | 7/2008 | Qian | A61N 7/02 600/439 |
| 2009/0076499 A1 * | 3/2009 | Azure | 606/41 |
| 2009/0076500 A1 * | 3/2009 | Azure | 606/41 |
| 2009/0076502 A1 * | 3/2009 | Azure et al. | 606/41 |
| 2009/0216175 A1 * | 8/2009 | Matsumura et al. | 604/20 |
| 2010/0081875 A1 * | 4/2010 | Fowler et al. | 600/114 |
| 2010/0100093 A1 * | 4/2010 | Azure | 606/34 |
| 2010/0228240 A1 * | 9/2010 | Henriksson | A61N 1/06 606/28 |
| 2011/0015630 A1 * | 1/2011 | Azure | 606/41 |
| 2011/0313229 A1 * | 12/2011 | Sugaya et al. | 600/1 |
| 2012/0232550 A1 * | 9/2012 | Azure | 606/41 |
| 2013/0035566 A1 * | 2/2013 | Mitragotri et al. | 600/309 |
| 2013/0079852 A1 * | 3/2013 | Henriksson | A61B 18/24 607/100 |
| 2013/0338477 A1 * | 12/2013 | Glossop et al. | 600/407 |

OTHER PUBLICATIONS

Baronzio and Hager, "Medical Intelligence Unit—Hyperthermia in Cancer Treatment: A Primer," Landes Bioscience and Springer Science+Business Media LLC; ISBN:0-387-33440-8 (2006).

Chan et al., "Electrically Stimulated Cell Membrane Breakdown in Human Placenta TL and Lung Cancer Cell A549 in 3D Trap Arrays on Si Substrate," *Device Research Conference*, pp. 103-104 (Jun. 23-25, 2003).

Chang, D.C., "Design of protocols for electroporation and electrofusion: Selection of electrical parameters," in D. C. Chang, B. M. Chassy, J. A. Saunders and A. E. Sowers. (Ed.Eds.), *Guide to Electroporation and Electrofusion*. Academic Press, Inc., San Diego, pp. 429-455 (1992).

Chang, D.C., "Structure and dynamics of electric field-induced membrane pores as revealed by rapid-freezing electron microscopy," in D. C. Chang, B. M. Chassy, J. A. Saunders and A. E. Sowers. (Ed.Eds.), *Guide to Electroporation and Electrofusion*. Academic Press, Inc., San Diego, pp. 9-27 (1992).

Coss et al., "Effects of Hyperthermia (41.5°) on Chinese Hamster Ovary Cells Analyzed in Mitosis," *Cancer Research* 39:1911-1918 (1979).

(56) References Cited

OTHER PUBLICATIONS

Cucullo et al., "Very Low Intensity Alternating Current Decreases Cell Proliferation," *GLIA* 51:65-72 (2005).

DeFord et al., "Effective Estimation and Computer Ccontrol of Minimum Tumour Temperature During Conductive Interstitial Hyperthermia," *Int. J. Hyperthermia* 7:441-453 (1991).

Haemmerich et al., "RF Ablation at Audio Frequencies Preferentially Targets Tumor—a Finite Element Study," *Proceedings of the Second Joint EMBS/BMES Conf.*, pp. 1797-1798 (Oct. 23-26, 2002).

Haemmerich and Wood, "Hepatic Radiofrequency Ablation at Low Frequencies Preferentially," *Int. J. Hyperthermia* 22:563-574 (2006).

Janigro et al., "Alternating Current Electrical Stimulation Enhanced Chemotherapy: a Novel Strategy to Bypass Multidrug Resistance in Tumor Cells," *BMC Cancer* 6:1-12 (2006).

Kirson et al., "Disruption of Cancer Cell Replicatioin by Alternating Electric Fields," *Cancer Res.* 64:3288-3295 (2004).

Kirson et al., "Alternating Electric Fields Arrest Cell Proliferation in Animal Tumor Models and Human Brain Tumors," *PNAS* 104:10152-10157 (2007).

Marmor et al., "Tumor Cure and Cell Survival After Localized Radiofrequency Heating," *Cancer Research* 37:879-883 (1977).

Miller et al., "Cancer Cells Ablation With Irreversible Electroporation," *Technology in Cancer Research & Treatment* 4:1-7 (2005).

Oleson et al., "Biological and Clinical Aspects of Hyperthermia in Cancer Therapy," *Am J. Clin. Oncol.* 11:368-380 (1988).

Pethig, R., "Dielectric Properties of Biological Materials: Biophysical and Medical Applications," *IEEE Trans. EI* 19(5): 453-473 (1984).

Proskuryakov et al., "Necrosis is an Active and Controlled Form of Programmed Cell Death," *Biochemistry (Moscow)* 67:387-408 (2002).

Rubinsky et al., "Irreversible Electroporation: a New Ablation Modality—Clinical Implications," *Tech. Cancer Res. Treatment* 6:1-12 (2007).

Shimm and Gerner, "Hyperthermia in the Treatment of Malignancies," in: Lehman, Justus F., *Therapeutic Heat and Cold* (Maryland, Williams & Wilkins), Ch. 14, pp. 674-699. ISBN 0-683-04908-9 (1990).

Stix, "Blockbuster—New Understanding of the Biology Behind a Successful Cancer Therapy May Lead to a Drug That Can Treat an Array of Solid Tumors," *Scientific American*, pp. 60-63 (May 2006).

Tello et al., "Electrochemical Therapy to Treat Cancer (In Vivo Treatment)," *Proceedings of the 20th Annual International Conference of the IEEE EMBS*, pp. 3524-3527 (Aug. 23-26, 2007).

Yi, "Cellular Ion Content Changes During and After Hyperthermia," *Biochem. Biophys. Res. Communic.* 91:177-182 (1979).

Zimmermann, U., "Electric field-mediated fusion and related electrical phenomena," *Biochim Biophys Acta* 694(3): 227-277 (1982).

Zimmermann, U., et al. "Transcellular ion flow in *Escherichia coli* B and electrical sizing of bacterias," *Biophys. J.* 13(10): 1005-1013 (1973).

Zimmermann, U., et al., "Rotation of cells in an alternating electric field: the occurrence of a resonance frequency," *Z Naturforsch* [C] 36(1-2): 173-177 (1981).

\* cited by examiner

IMMUNE MEDIATED CANCER CELL DESTRUCTION, SYSTEMS AND METHODS

CROSS-REFERENCES TO RELATED APPLICATIONS

The present application claims priority to U.S. Provisional Application Ser. No. 61/328,580 filed Apr. 27, 2010 the full disclosure of which is incorporated herein by reference.

BACKGROUND OF THE INVENTION

The present invention relates generally to electric field delivery to a tissue of a patient. More particularly, the present invention provides systems and methods for delivering electric fields to a target tissue of a patient for destruction of cancerous cells and eliciting or induction of a specific anti-cancerous cell immune response in the patient.

The immune system is the body's natural defense against infection and disease, destroying foreign elements such as harmful bacteria and viruses that enter the body. In order for the immune system to provide effective defense against disease, it has to recognize and label agents that are "foreign" and distinguish foreign infection from the body's own non-harmful cells and components. Once this happens, cells in the immune system can function to eliminate the foreign agents.

Another important role of the immune system is to identify and eliminate tumors. The transformed cells of tumors include proteins or antigens that are not found on normal cells. To the immune system, these antigens appear foreign, and their presence causes immune cells to attack the transformed tumor cells. The antigens produced by tumors can have several sources, and may include those derived from a foreign infecting agent, such as a virus, as well as the body's own proteins that have been mutated or altered, or proteins that occur at low levels in normal cells but reach high levels in tumor cells.

One primary response of the immune system to tumors is to destroy the abnormal cells using so called natural killer T cells, sometimes with the assistance of other immune cells, such as helper T cells. Tumor antigens may be processed and presented by immune cells in a similar way to viral or bacterial antigens. This allows immune cells such as killer T cells to recognize the tumor cell as abnormal. In addition, in some instances antibodies are generated against tumor cells allowing for their destruction by the complement system.

While the immune system represents a powerful and vital defense against cancer, in some cases, tumors evade the immune system and go on to become cancers. Thus, there is great interest in cancer immunotherapy treatments and techniques that utilize or stimulate the body's own immune system to better combat and eradicate cancerous cells in the body. Cancer immunotherapy aims to teach the body's own natural defenses to identify cancer cells correctly and then kill them. There are different types of cancer immunotherapy, including cancer vaccines and a treatment called Antigen-Specific Cancer Immunotherapeutics (ASCI).

While cancer immunotherapy holds tremendous promise, to date very few effective treatments have been developed. Thus, there is continued interest in techniques and treatments that can stimulate a patient's immune system to better combat cancerous cell growth.

BRIEF SUMMARY OF THE INVENTION

Systems and methods are provided for delivering electric fields to a target tissue of a patient for destruction of cancerous cells so as to elicit or induce a specific anti-cancerous cell immune response in the patient. Methods include establishing an electrical current flow through a volume of the target tissue so as to preferentially destroy cancerous cells in the volume.

Thus, in one aspect, the present invention includes systems and related methods for delivering electric fields to a target tissue of a patient for destruction of cancerous cells, including establishing an electrical current flow through a volume of the target tissue so as to preferentially destroy cancerous cells in the volume and induce a specific host anti-cancerous cell immune response. The electrical current flow can be selected such that thermal based protein coagulation and denaturation in the cancerous cells or tissue is minimized or substantially avoided. Administering an immunostimulatory agent or adjuvant can further be accomplished.

In another aspect, the present invention further includes methods including identifying a first target tissue site and a second target tissue site; eliciting destruction of cancerous cells of the first target tissue site comprising establishing an electrical current flow through a volume of the second target tissue so as to preferentially destroy cancerous cells in the volume and induce a specific host anti-cancerous cell immune response so as to control growth of cancerous cells at a location remote from the second target tissue that have not directly received electrical current flow. In some instances, cancerous cells will have been seeded at the second target tissue site.

The present invention further includes systems and methods for delivering electric fields to a target tissue of a patient for destruction of cancerous cells, including identifying a first target tissue site and a second target tissue site; eliciting destruction of cancerous cells of the first target tissue site including establishing an electrical current flow through a volume of the second target tissue so as to preferentially destroy cancerous cells in the volume; removing tissue or fluid from the second target tissue following electrical current application; delivering to the first target tissue site the tissue or fluid removed from the second target tissue, so as to reduce growth of cancerous cells at a location remote from the second target tissue that have not directly received electrical current flow.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
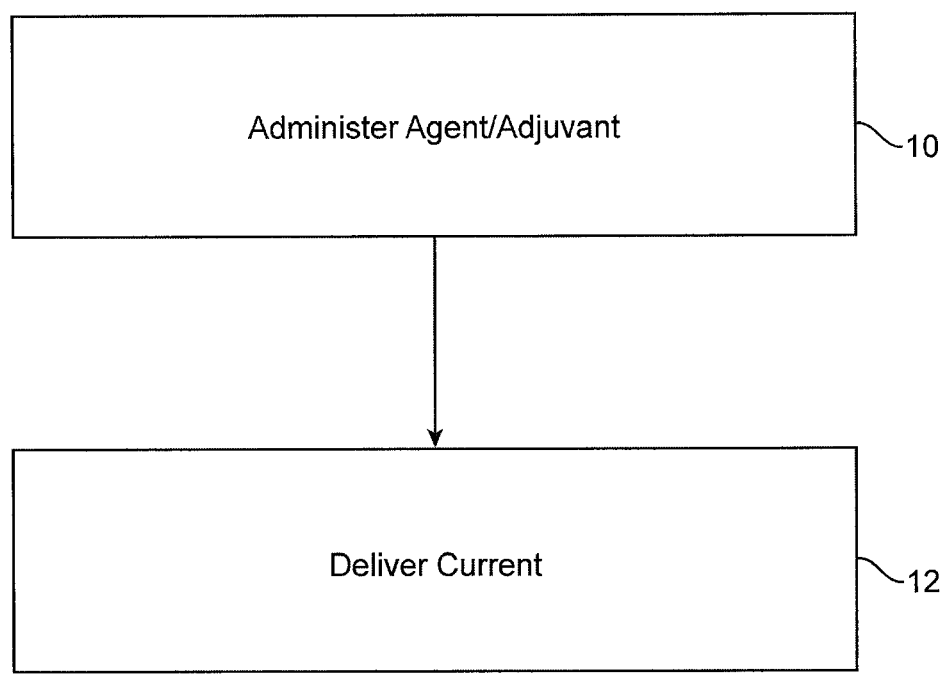
FIG. 1 illustrates a method according to an embodiment of the present invention.

The present invention provides methods, and related systems and devices, for destruction of cancerous cells in a patient. According to the present invention, an electric field is applied to a target tissue region for controlled and/or preferential destruction of cancerous cells, and stimulation in vivo of the patient's own immune system against cancerous cells in the patient's body. In particular, application of electric fields or energy delivery as described herein may be selected to stimulate an adaptive or specific immune response in the patient for destruction of cancerous cells in the patient's body, including cancerous cells at or near the treatment site as well as cancerous cells at locations in the patient's body separate or remote from the energy delivery treatment site.

Energy application and delivery according to the present invention includes establishing current flow through a target tissue that can include a controlled low-level tissue heating or mild hyperthermia. Current flow can be established between electrodes, e.g., in a bipolar arrangement, with current flow established and substantially contained between the spaced electrodes. Tissue heating can be more precisely controlled to prevent or minimize excessive heating and/or hot spots that can cause indiscriminate tissue destruction and undesired damage to healthy or non-target tissues. While heating may occur with energy application according to the present invention due to tissue resistance and, to a lesser degree, frictional heating, high temperature thermal ablation or thermally-induced coagulation, protein denaturation, and/or cross-linking as is typically present with conventional high-temperature thermal RF ablation is generally avoided with the present methods.

As thermally-induced coagulation/cross-linking is substantially avoided, antigenic properties of cancerous cell specific proteins may be better preserved in the current treatment methods compared to conventional high-temperature thermal ablation techniques. In addition to disrupting the viability and/or integrity of cancerous cells, energy delivery treatment according to the present invention can elicit migration of immune cells to the treated target tissue region. Histopathology analysis has identified immune cells such as macrophages increasingly present about the target tissue following energy application, indicating an immune cell mediated response is elicited by the current application. In conjunction with energy application according to the current methods, degradation (e.g., enzymatic cleavage) and/or processing (e.g., immune cell mediated processing) of cancerous cell proteins may lead to generation of an in vivo specific immune response for further destruction of cancerous cells that may occur not only at or about the treatment site, but also at locations remote or removed from the energy delivery site.

Stimulation of an immune response, including a cancer specific response, according to the present invention can provide a powerful tool for treatment and/or targeted destruction of cancerous cells and tissue in a patient. As such, methods and structures as described herein can make use of this previously unrecognized immune mediated action, including treatment planning tools and approaches, treatment of previously non-accessible or lesser accessible treatment sites, use of immunostimulating agents and/or adjuvants, and the like to greatly enhance cancerous cell destruction approaches.

Energy delivery as described has been observed to be surprisingly effective in preferentially damaging and destroying cancerous cells compared to non-cancerous or healthy cells/tissue. Preferential destruction, as described herein, refers to establishing current flow as described herein such that cytotoxic effects of treatment are, on average or as a whole, more destructive and/or lethal to cancerous or hyperplastic cells (e.g., cells exhibiting or predisposed to exhibiting unregulated growth) compared to non-cancerous or healthy cells. In some instances, establishing current flow and induction of low or mild hyperthermia as described herein is remarkably effective in preferentially destroying cancerous cells with limited or no observable damage to non-cancerous tissues.

Without being bound by any particular theory, electrode configuration and field application as described in certain embodiments (e.g., radially and/or in a plurality of different directions) may take advantage of tumor or mitotic cell physiology to increase treatment effectiveness, and can include a more optimal or effective orientation of the applied field with respect to dividing cells of the target region. For example, energy application can be accomplished such that current fields are substantially aligned at some point during energy delivery with division axes of dividing cells (e.g., cancerous cells), thereby more effectively disrupting cellular processes or mitotic events (e.g., mitotic spindle formation and the like). As cancerous cells are dividing at a higher rate compared to non-cancerous cells, field application in this manner may preferentially damage cancerous cells compared to healthy or non-dividing cells. It will be recognized, however, that energy application according to the present invention likely has several or numerous cytotoxic effects on cells of the target region and that such effects may be cumulatively or synergistically disruptive to a target cell, particularly to cells disposed or pre-disposed to unregulated growth (i.e., cancerous cells). Other cytotoxic or disruptive effects of the energy application as describe herein may occur due, for example, to application of mild hyperthermia (e.g., mild heating of tissue between about 40 to 48 degrees C.; or less than about 50 degrees C.); ion disruption, disruption of membrane stability, integrity or function; disruption of cellular components and/or organelles; and the like.

As noted, the energy delivery according to the present invention in some instances has been observed to be preferentially cytotoxic or destructive of cancerous cells while substantially sparing the non-cancerous cells, such as normal stromal tissue including fibrous connective tissue, arterioles, capillaries, veins, lymphatic vessels, smooth muscle stroma, and nerves. The applied treatment currents are controlled so the tissue within the treatment array does not substantially include high-temperature, thermally ablative temperatures, and therefore the proteins of the cell are not substantially thermally coagulated (denatured by high-heat induced cross-linking) during current application. Without being bound by any theory, current application and cell destruction according to the current methods may elicit the release from target cells of endogenous enzymes, especially from lysosomes within the cell, lead to some autodigestion of the cancer cells. These endogenous enzymes may cleave the cancer cells non-denatured proteins into fragments that can in turn be taken up by macrophages and dendritic cells, leading to the stimulation of both a humeral and cellular immune response against the patients own tumor.

Further, without being bound by any particular theory, treatment resulting autodigestion and release of enzymatically cleaved, non-denatured protein fragments may be taken up and processed by immune cells, such as taken up by macrophages initially and subsequentially dendritic cells. These cells continue the fragmentation of the proteins into antigenic peptides and the dendritic cells display the antigens on their surfaces. Antigen-bearing cells, such as dendritic cells, travel to lymph nodes and the spleen via the lymph system, where they interact with B cells, which produce antibodies, and killer T cells, which are directed against the tumors from which the antigens were derived. In energy application according to the present invention, the vascular system of the target region typically remains substantially intact following treatment, including the lymph vessels, making it easier and more efficient for the cells to travel to the lymph nodes and spleen, than by treatments that destroy the vascular system. Antigen presenting cells, such as dendritic cells, present their antigen-laden MHC molecules to naive helper T cells. The dendritic cells can program the naive helper T cells to recognize an antigen as foreign and as a hazard to the patient's body. The programmed helper T cells then prompt the B cells to produce antibodies that can bind to surface antigens expressed by the tumor cells. The dendritic cells and helper cells also activate killer T cells, which can destroy tumor cells expressing these surface antigens. Whether the patients immune system responds with antibodies or killer cells seems to be determined in part by which subset of dendritic cells conveys the message and which of two types of immune-stimulating cytokines they prompt the helper T cells to make.

Furthermore, it is possible that the current delivery as described herein alters or disrupts immunotolerogenic signaling in the patient that permits the cancerous tissue to substantially escape immunosurveillance in the absence of current treatment as described. One reason that tumors, in general, may escape immunosurveillance is that they express tolerogenic signals that suppress immunity. It is possible that damage associated with sumor-specific injury resulting from current delivery according to the present invention will result in an immunogenic response due at least partially to a change in signaling associated with the form of cell death induced by the current field. Change in signaling can include changes to intercellular signaling as well as intra and extracellular signaling. Moreover, the current field per the present invention may induce (e.g., directly) certain genomic changes associated with immunostimulation—e.g., such as heat shock proteins induced by the current field, which may be implicated in increasing antigen presentation (e.g., by dendritic cells) or in interactions between dead/dying cells and dendritic cells. Current field delivery and stimulation or eliciting of an adaptive or specific immune response according to the present invention may include one or more of the mechanisms of action described herein, or none, and/or may include additional processes not specifically listed herein.

Appropriate adjuvants and/or immunostimulants in conjunction with energy delivery according to the present invention can be used to increase the type and level of immune response to the tumor antigens. Tumor cells, being abnormal, may generate aberrant molecules/peptides and peptides in different amounts, which could be targeted by the stimulated immune system. Antigens that occur only on cancerous cells are difficult to find, but several have been isolated by researchers for some types of cancer. For example, adjuvants can be injected locally within the tumor at or about the time of treatment. Adjuvant injection, together with the non-specific aberrant fragmentation of proteins by autodigestion non-denatured tumor cell protein fragments produced in response to energy delivery as described, may increase the in vivo activity of the immune system against a patients own tumors.

Thus, the present invention includes methods and related structures for delivering electric fields to a target tissue of a patient so as to induce a specific host anti-cancerous cell immune response. Current delivery as described herein can elicit destruction of cancerous cells locally or proximate to the current delivery site, and may further elicit or stimulate a host immune response that induces a specific immune response further destructive of cancerous cells at the current delivery site or a second/remote site, or both. Current delivery methods and structures can be tailored or configured to take advantage of the induced immune response. For example, as noted above, current delivery can be coupled or coordinated with delivery or administration of an immunostimulatory agent or adjuvant. Further, immune response induction as described herein can be utilized in treatment planning or selection of current delivery location.

Referring to FIG. 1, a method of delivering or administering an immunostimulatory agent or adjuvant and current is described. The method includes administering an immunostimulatory agent or adjuvant (Step 10) and delivering current to a target site (Step 12). Agent administration and current delivery can occur in any order, may be simultaneous or substantially simultaneous, immediately successive in time or have some delay between steps. Current delivery can be accomplished by a number of means, including those delivery methods and structures described herein.

One or more agents, e.g., immunostimulatory agents and/or adjuvants, can be delivered as described, and may be coupled with or coordinated with energy or current delivery. An immunostimulatory agent will generally include agents that increase a number of T cells (e.g., stained or detectable T cells) as a result of delivery (e.g., in vitro or in vivo), whereas a decrease (or lack of increase) in T cell proliferation or number of detectable T cells will generally indicate that an agent is not effective as an immunostimulatory agent. An adjuvant or immunostimulatory agent is a pharmacological or immunological agent that modifies the effect of immunization of a patient receiving energy treatment described herein. Adjuvants or agents can be added to enhance, stimulate, or facilitate the patient's immune response, including a cancer specific response following energy/current delivery as described herein. Various adjuvants, including those known in the art, can be utilized herein with energy or current delivery techniques. Non-limiting examples of adjuvants include aluminum salts (e.g., aluminum hydroxide or aluminum phosphate), Freund's complete adjuvant (FCA) and incomplete adjuvant, or organic adjuvants (e.g., squalene).

Figure 2:
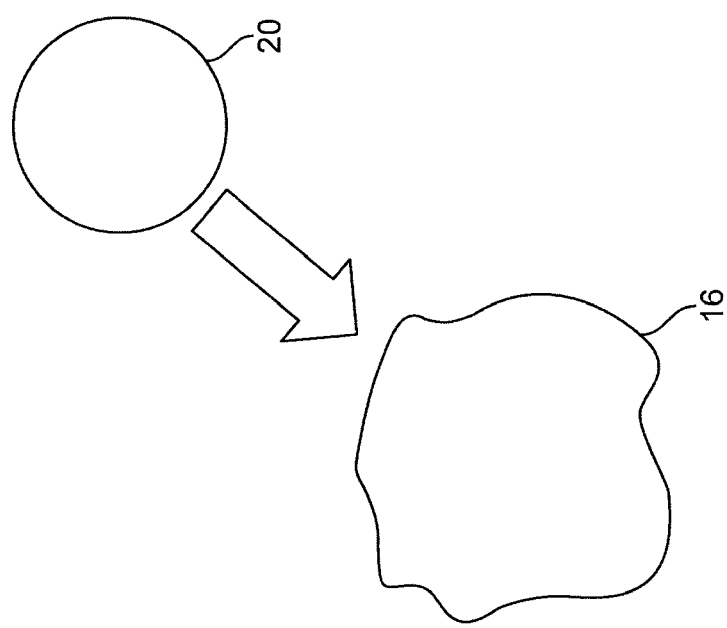
FIG. 2 illustrates current delivery at a first site and eliciting a response at a second site, according to an embodiment of the present invention.
Figure 2:
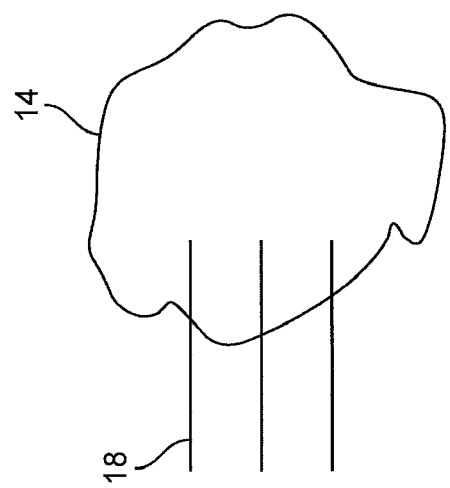

As indicated, energy or current deliver as described herein may elicit destruction of cancerous cells locally or proximate to the current delivery site, and may further elicit or stimulate a host immune response further destructive of cancerous cells at the current delivery site or a second/ remote site, or both. FIG. 2 illustrates energy delivery at a first site 14 eliciting or stimulating an immune response 20 at a second site 16. As shown, energy or current delivery can include positioning one or more electrodes 18 in tissue at a first target site 14, and delivery of current to the target tissue (see also, below). As described, energy delivery can further elicit a host specific immune response 20 further destructive to the cancerous cells. Such an immune response may not only effect cancerous cell survival at the first site 14, but may also elicit immune cell mediated destruction of similar cancerous cells at a second site 20.

Such a response that is more systemically oriented or not necessarily limited only to the initial target site of energy/current delivery can be utilized for selection of current delivery and/or treatment planning. For example, in some instances where multiple cancerous tissues or tumors are present, certain cancerous sites may be more accessible or more sensible targets than others and may be the initial target of current delivery at a particular stage of treatment. Thus, a phase of treatment may include selecting one or more cancerous sites for current/energy delivery as opposed to others. For example, cancerous sites or tumors may be present in proximity to sensitive tissues or difficult to access locations, or otherwise less attractive for probe placement and/or energy delivery. Treatment planning and selection of energy delivery can be coupled with other imaging and detection methods, and may factor in an immune mediate response as indicated.

Figure 3:
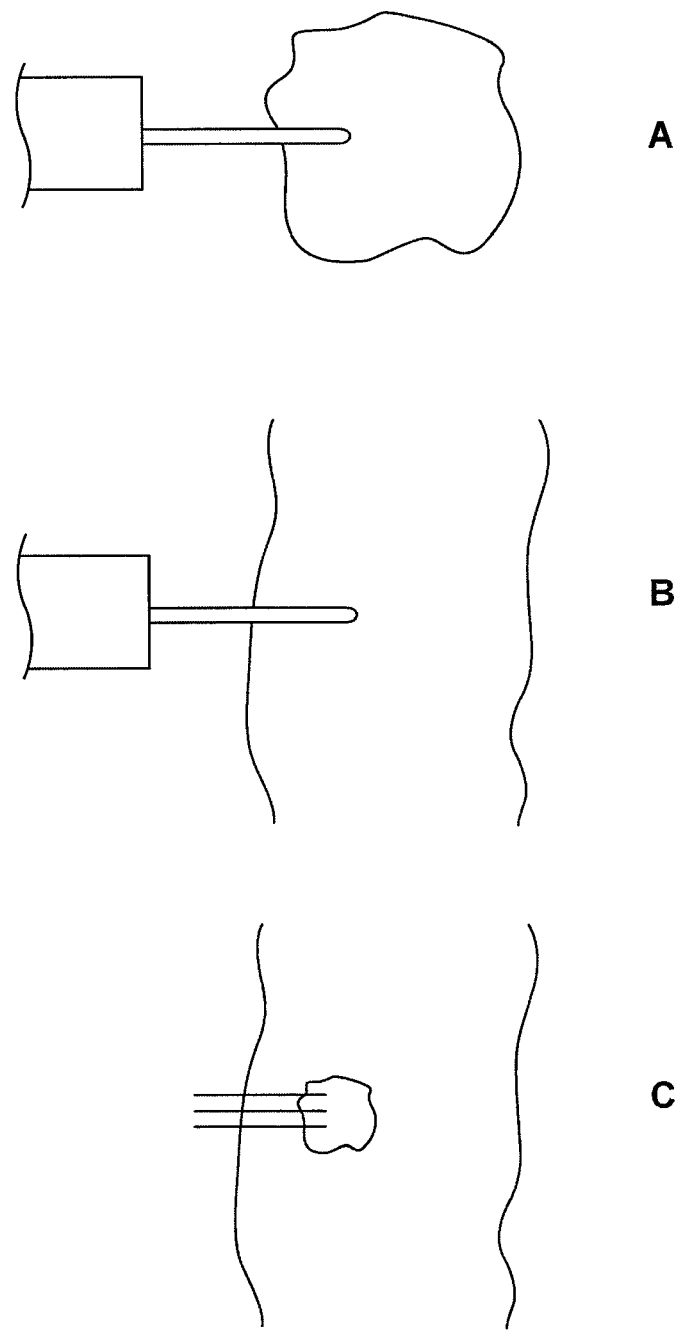
FIGS. 3A through 3C illustrate seeding cells from a first site at a second location, according to an embodiment of the present invention.

In another embodiment, remote targeting via an immune mediate response can include biopsy and seeding of cancerous tissue or cells in a patient, with energy delivery at the seeded site so as to elicit an immune mediate response at a location remote from the seeded site. Biopsy and seeding, according to an embodiment of the present invention, is described with reference to FIGS. 3A through 3C. Cancerous cells are obtained from a first site (FIG. 3A) and implanted or seeded at a second location (FIG. 3B). Energy delivery is accomplished in a grown tissue mass at the second location (FIG. 3C). Energy delivery at the second location may elicit a more systemic or non-locally constrained immune response in the patient, which can be destructive of cancerous cells remote from the second location.

Various energy delivery systems, which can include a wide array of selected electrode or probe configurations, can be utilized according to the present invention for energy or current delivery. Delivery systems and methods can be utilized, modified, or tailored to take further advantage of an immune response elicited following current delivery as described herein. For example, energy delivery systems may be utilized in conjunction with systems for administering or delivering an immunostimulatory agent or adjuvant. Energy delivery systems may further or alternatively be modified or configured for delivery of both current to the tissue as well as delivery of an agent or adjuvant.

In one embodiment, electrodes can include an array of needle-type electrodes, which can be fixed to common support (e.g., housing) or separately positionable and controlled. Such a plurality or array of electrodes can include a straight-needle array including electrically conductive material such as stainless steel, gold, silver, etc. or combination thereof. An array of straight-needle electrodes can be coupled to a rigid needle support or housing that can ensure correct positioning of each individual needle relative to the others. The needles can be arranged parallel to one another with opposing rows and/or columns of electrodes ensuring the field is delivered to and contained within the target area. Needle length and needle spacing can vary depending on the actual dimensions of the target tissue. Individual needle placement can be guided using imaging (e.g., ultrasound, X-ray, etc.) and relative needle position can be maintained with a rigid grid support (e.g., housing, template, etc.) that remains outside the body. The needle assembly will electrically connect to the control system or module, e.g., via insulated wires and stainless steel couplings.

In another embodiment, a probe can include one or more electrodes that are deployable from an elongate probe housing or catheter. Such embodiments may be particularly useful for treatment of target areas more difficult to access with an array of fixed needles. Such deployable type probes, and others described herein, can be inserted percutaneously through the skin of the patient and into the target tissue, or advanced through a body lumen. As above, appropriate imaging technology can be used to guide the precise placement of the probe in the target site. In one embodiment, a deployable type probe can include outer polyurethane sheath housing pre-shaped deployable shape memory metal tines and a stainless steel central electrode tip. Conductive surfaces can further be coated with a highly conductive material.

Another embodiment of the probe can include one or more expandable elements (e.g., balloon) that can be individually positioned around a target area or organ, or advanced in a body lumen, and then deployed and "inflated" to achieve maximum surface area and optimal distribution of the therapeutic field. In one example, an electrically active segment of the expandable element can include an electrically conductive material (e.g., silver, gold, etc.) coated or deposited on a mylar balloon. Prior to deployment and inflation, the expandable element can be contained inside a flexible catheter that can be guided to the treatment area. Once the delivery catheter is positioned, the "balloon" can be deployed and expanded via the circulation of fluid through the balloon, which can have a selected or controlled temperature and may act as a heat sink. The therapeutic field can than be delivered via the silver coating on the mylar balloon. Two or more probes deployed in this fashion will serve to contain the field within the treatment area.

Electrodes and probes of the present invention can be coupled to control system or control module designed to generate, deliver, monitor and control the characteristics of the applied field within the specified treatment parameters. In one embodiment, a control system includes a power source, an alternating current (AC) inverter, a signal generator, a signal amplifier, an oscilloscope, an operator interface and/or monitor and a central processing unit (CPU). The control unit can manually, automatically, or by computer programming or control, monitor, and/or display various processes and parameters of the energy application through electrodes and to the target tissue of the patient. While the control system and power source can include various possible frequency ranges, current frequency delivered to target tissue will be less than about 300 kHz, and typically about 50 kHz to about 250 kHz (e.g., 100 kHz). Frequencies in this range have been observed as effective in precisely controlling the energy application to the target tissue, controlling thermal effects primarily to mild thermal application, and preferentially destroying cancerous cells with limited or no observable damage to non-cancerous tissues.

Energy application according to the present invention can include mild or low levels of hyperthermia. In some embodiments, small changes/elevations in temperature in the target tissue region may occur, generally ranging from about 0-15 degrees (and any number therebetween) above pre-treatment tissue temperature. Typically, temperature elevations will be no more than about 10 degrees C. above body temperature, and may be about 2 degrees to less than about 10 degrees C. above body temperature (e.g., normal human body temperature of about 38 degrees C.). Thus, local tissue temperatures (e.g., average tissue temperature in a volume of treated tissue) during treatment will typically be less than about 50 degrees C., and typically within a range of about 40-48 degrees C. In one embodiment, average target tissue temperature will be selected at about 42-45 degrees C. As target tissue temperatures rise above about 40-42 degrees C. during treatment, the cytotoxic effects of energy delivery on cancerous cells of the target region are observably enhanced, possibly due to an additive and/or synergistic effect of current field and hyperthermic effects. Where mild hyperthermic effects are substantially maintained below about 48 degrees C., the energy delivery according to the present invention appears to more preferentially destroy cancerous cells compared to healthy or non-cancerous cells of the target tissue region. Where energy delivery induces tissue heating substantially in excess of about 45-48 degrees C. (e.g., particularly above 48-50 degrees C.), the preferential cytotoxic effects on cancerous cells may begin to diminish, with more indiscriminate destruction of cancerous and non-cancerous cells occurring.

Tissue temperatures can be selected or controlled in several ways. In one embodiment, tissue temperatures can be controlled based on estimated or known characteristics of the target tissue, such as tissue impedance and tissue volume, blood flow or perfusion characteristics, and the like, with energy application to the tissue selected to deliver an approximated controlled mild increase in tissue temperature. In another embodiment, tissue temperature can be actively detected or monitored, e.g., by use of a feedback unit, during treatment, with temperature measurements providing feedback control of energy delivery in order to maintain a desired target tissue temperature or range. Temperature control measures can include electronics, programming, thermosensors and the like, coupled with or included in a control unit or module of a system of the invention. Further, use of inflatable/expandable balloons and circulation heated/cooled inflation media further facilitates control and delivery of the desired treatment temperature to the target tissue.

Energy application and induction of hyperthermia in a target tissue region according to the present application can include delivery of various types of energy delivery. As described, application of generally intermediate frequency range (e.g., less than about 300 kHz) alternating current in the RF range has been observed as effective in establishing mild heating and hyperthermia, as well as current fields in a controlled manner so as to provide a cytotoxic effect, and in some instances, a preferential destructive effect to cancerous cells of a target tissue volume/region. It will be recognized, however, that additional energy applications and/or ranges may be suitable for use according to the present invention, and that systems and methods of the present invention may be amenable to use with other or additional energy applications. For example, energy application can include current flow having frequencies found generally in the RF range, as well as microwave range, including higher frequencies such as 300-500 kHz and above, and may further be amenable to use with direct current applications. Applied current can be pulsed and/or continuously applied, and energy delivery can be coupled with a feedback-type system (e.g., thermocouple positioned in the target tissue) to maintain energy application and/or tissue heating in a desired range.

In certain embodiments, particularly where energy application is selected for lower power delivery/ablation, the control system can be designed to be battery powered and is typically isolated from ground. AC current is derived from the integrated power inverter. An intermediate frequency (e.g., less than 300 kHz; or about 50 kHz to about 250 kHz) alternating current, sinusoidal waveform signal is produced from the signal generator. The signal is then amplified, in one non-limiting example to a current range of 5 mA to 50 mA and voltage of up to 20 Vrms per zone. Field characteristics including waveform, frequency, current and voltage are monitored by an integrated oscilloscope. Scope readings are displayed on the operator interface monitor. An integrated CPU monitors overall system power consumption and availability and controls the output of the signal generator and amplifier based on the treatment parameters input by the operator. The operator can define treatment parameters to include maximum voltage, maximum current or temperature, maximum power, and the like.

Imaging systems and devices can be included in the methods and systems of the present invention. For example, the target tissue region can be identified and/or characterized using conventional imaging methods such as ultrasound, computed tomography (CT) scanning, X-ray imaging, nuclear imaging, magnetic resonance imaging (MRI), electromagnetic imaging, and the like. In some embodiments, characteristics of the tumor, including those identified using imaging methods, can also be used in selecting ablation parameters, such as energy application as well as the shape and/or geometry of the electrodes. Additionally, these or other known imaging systems can be used for positioning and placement of the devices and/or electrodes in a patient's tissues.

Figure 4:
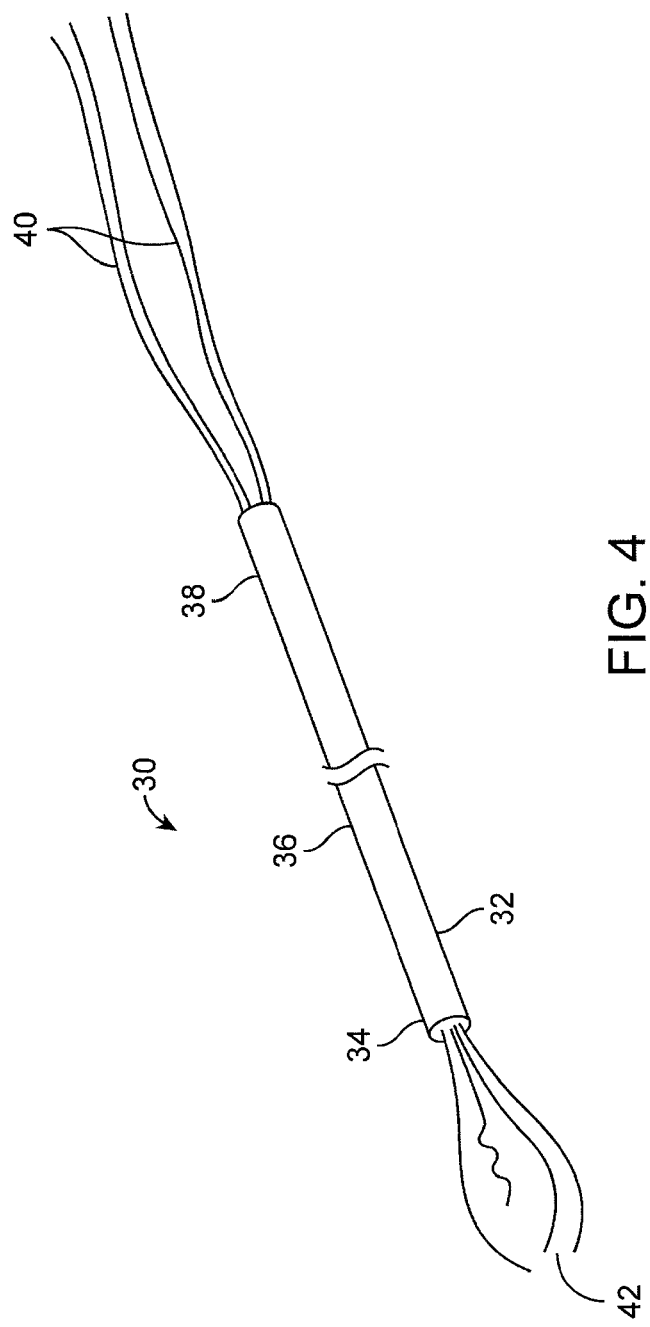
FIG. 4 illustrates a probe or device according to an embodiment of the present invention.

Referring to FIG. 4, a device according to an embodiment of the present invention is described. The device 30 includes a delivery member 32 having a distal portion 34 and a proximal portion 36. The device 30 further includes a proximal portion 38 of the device that can be coupled (e.g., removably coupled) to the delivery member 32. Additionally, the device 30 can include conductive cables 40 electrically coupled to an energy source (not shown). The device includes a plurality of electrodes 42 at the distal portion 34 of the delivery member 32. The electrodes 42 can be positioned or fixed, for example, at the distal end of the delivery member 32 or positionable and deployable from a lumen of the delivery member 32 and retractable in and out of the distal end of the delivery member 32. The electrodes 42 can include a non-deployed state, where the electrodes 42 can be positioned within a lumen of the delivery member 32, and a deployed state when advanced from the distal end of the delivery member 32. Electrodes 42 are advanced out the distal end and distended into a deployed state substantially defining an ablation volume.

Figure 5A:
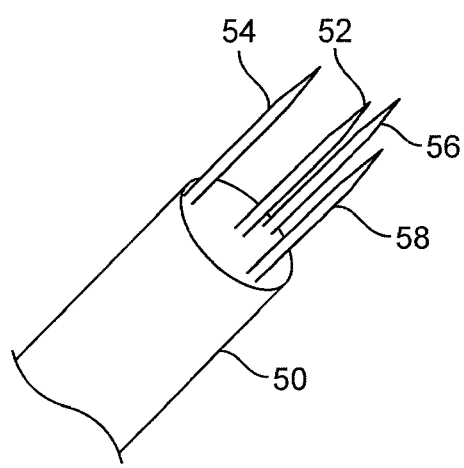
FIGS. 5A through 5D illustrate a probe or device according to another embodiment of the present invention.
Figure 5C:
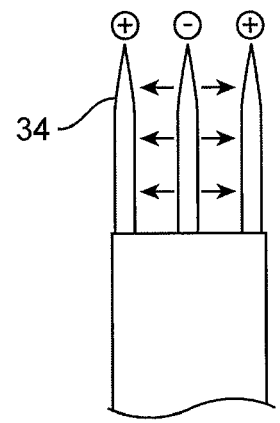
Figure 5B:
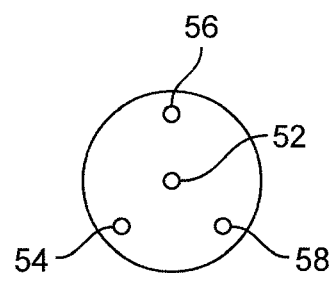
Figure 5D:
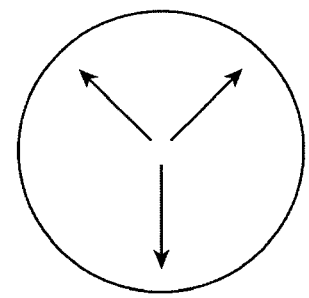

In another embodiment, a probe can include a plurality of needle electrodes fixed to or positioned on a body or housing of a device. FIGS. 5A through 5C show a device having a plurality of electrodes coupled to a housing, according to another embodiment of the present invention. As shown, the device 50 includes a plurality of electrodes extending from the distal portion (e.g., housing) of the device. FIG. 5A shows a three dimensional side view of the device having the plurality of electrodes. FIG. 5B shows a top view of the device illustrating the electrode arrangement. The plurality includes a centrally positioned electrode 52 and outer electrodes 54, 56, 58 spaced laterally from the central electrode 52. The illustrated electrodes include substantially linear needle-like portions or needle electrodes. The electrodes extend from the distal portion of the device and are oriented to be substantially parallel with the longitudinal axis of the device 50. Additionally, each electrode is substantially parallel with other electrodes of the plurality. The plurality of electrodes substantially define the ablation volume, with the outer electrodes 54, 56, 58 substantially defining a periphery of the ablation volume and the electrode 52 positioned within or at about the center point of the defined periphery. Each of the electrodes can play different roles in the ablation process. For example, there can be changes in polarity and/or polarity shifting between the different electrodes of the device. As with other devices of the invention, electrodes can be electrically independent and separately addressable electrically, or two or more electrodes can be electrically connected, for example, to effectively function as one unit. In one embodiment, for example, outer electrodes 54, 56, 58 can be electrically connected and, in operation, include a polarity different from that of the inner electrode 52. As illustrated in FIG. 5C the electrodes 52 and 54, 56 of the device can include opposing charges (e.g., bipolar). In such an instance, the applied electrical current can provide an electrical field, as illustrated by the arrows, extending radially outward from the central electrode 52 and toward the peripherally positioned or outer electrode(s) 54, 56. FIG. 5D illustrates the concept of a current flow center, where current flow is established through about a center location of a treatment volume.

In some embodiments, electrodes can be deployable from small, electrode guides or positioning tubes, e.g., microtubes or microcatheters, positionable in and advanceable from a distal portion of an ablation probe. The terms catheter or microcatheter, as used herein, refer generally to an elongate tube having a lumen. For example, an ablation probe of the present invention can include a distal portion or a delivery member having a lumen with electrode aiming/positioning microtubes/microcatheters positioned within the lumen of the delivery member, with electrodes disposed in the microcatheters and deployable therefrom. Both microcatheters and electrodes can include a shape memory metal and include a preformed shape for deployment.

Figure 6A:
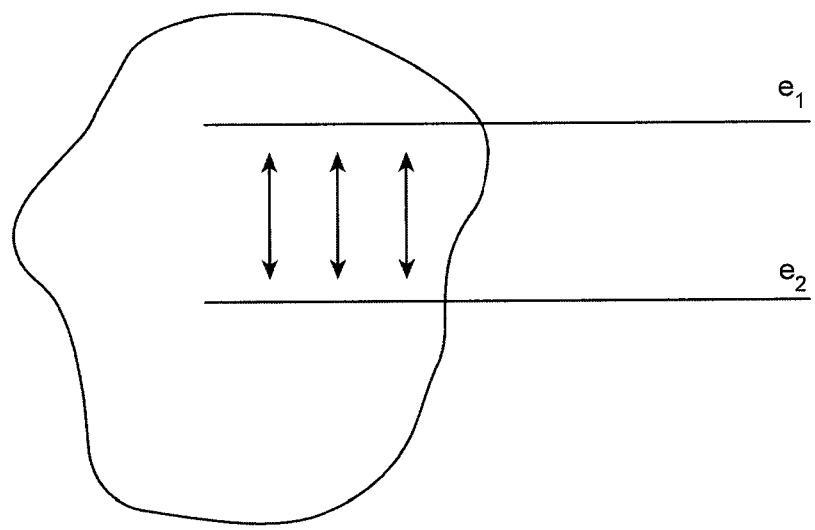
FIGS. 6A through 6D illustrate current or field delivery in a target tissue according to various embodiments of the present invention.
Figure 6B:
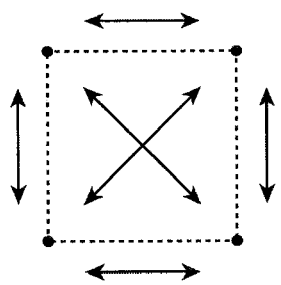
Figure 6C:
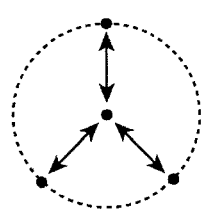

Energy delivery between positioned electrodes is further described with reference to FIGS. 6A through 6C. Electrodes can be positioned in a target tissue and activated in pairs or groups such that the desired electric field is delivered to the target tissue between the electrodes and, in some instances, in a radial orientation or in a plurality of different directions. FIG. 6A conceptually illustrates establishment of a current field with two spaced electrode elements ($e_1$ and $e_2$) as a basic field delivery unit according to an embodiment of the present invention. As shown, distal portions of two electrodes ($e_1$ and $e_2$) of a plurality positioned in a target tissue and activated as an electrode pair or circuit, with the applied current substantially contained between the two. Thus, electrodes can be activated in a bipolar configuration, with current flowing between electrodes (e.g., between $e_1$ and $e_2$) and the tissue between the electrodes acting as a flow medium or current pathway between the electrodes. Positioning and activation of pairs or relatively small groups of electrodes in this manner allows more precise control of the current applied to the tissue, containment of the applied field to the desired location, as well control of heating or limited temperature increase in the target tissue.

Figure 6D:
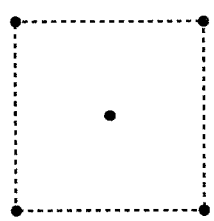

In some embodiments of therapeutic energy delivery according to the present invention, electrode positioning and/or device configuration advantageously allows delivery of field throughout a target tissue volume in a plurality of different directions, such as radial field orientation and application through the target volume. FIGS. 6B through 6D illustrate simplified plan views of electrode positioning and spacing for field application according to exemplary embodiments of the present invention. As shown in FIG. 6B, a simple four electrode grouping can be selected for use in treatment, with an applied field established between groups or pairs (e.g., different opposing electrode pairs). Groups or pairs of different electrodes can be differentially activated for field application in different directions/orientations. Electrode positioning can further include outer electrodes substantially defining a volume, and an electrode positioned within the volume. Electrode activation can include application of current flowing between a centrally positioned electrode and outer or secondary electrodes positioned spaced from the inner or center electrode. Thus, an exemplary delivery unit can include an inner or centrally located electrode surrounded by spaced electrodes, with the applied field extending between the central electrode and the outer spaced electrodes. In this manner, the outer electrodes can essentially define an ablation volume with the inner/central electrode positioned within the volume. Field delivery in this way is advantageously controlled and substantially contained within the ablation volume. Furthermore, field delivery in this manner advantageously allows a current field to be established with current flow in a radial and plurality of different directions through the treatment volume, e.g., extending through or from a flow center located about the centrally positioned electrode. FIG. 6C illustrates exemplary electrode positioning including outer electrodes and an inner or centrally located electrode, for defining a discrete target tissue volume for treatment and application of treatment filed extending radially through the volume. Electrode positioning will not be limited to any particular configuration, and various arrangements will be possible.

In another embodiment of the present invention, systems and methods can include a plurality of electrodes (e.g., needle electrodes) that can be individually advanced and positioned in the target tissue, and electrically activated for energy delivery. In such an embodiment, an array of electrodes can be advanced through the tissue of the patient and electrically activated (e.g., differentially activated) to deliver current field in a plurality of different directions. An array or plurality as described can include various numbers of electrodes, and the selected number can depend, at least partially, on factors such as target tissue characteristics, treatment region, needle size, and the like. An array can include a few to several dozen electrodes. In one example, an array can include about a few electrodes, to about a dozen or hundred, or more (e.g., 10-100, 5-200, any number therebetween, or more) electrodes for positioning in the target tissue region.

Figure 7A:
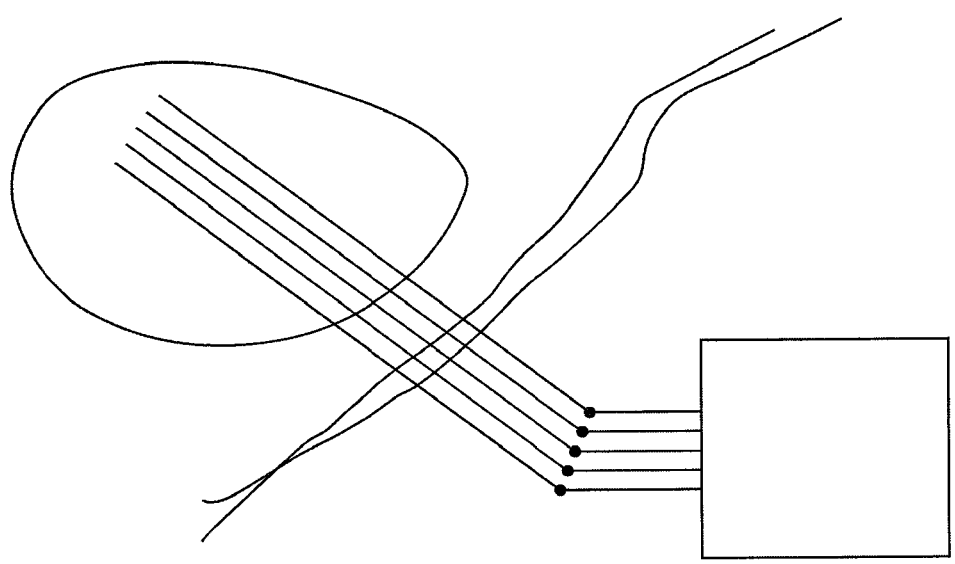
FIGS. 7A and 7B illustrate a system for delivery of electric fields to a tissue of a patient using a plurality or array of electrodes.
Figure 7B:
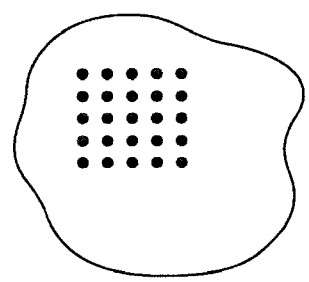

A system and method for delivering electric fields according to the present invention is described with reference to FIGS. 7A and 7B. The system includes a plurality of individual needle electrodes that can be positioned in a target tissue. Elongated needle electrodes will include a distal portion and a proximal portion. The proximal portion of each electrode will be electrically connected to a system control unit or module, which includes electronics, storage media, programming, etc., as well as a power generator, for controlled delivery of selected electrical fields to the target tissue. In use, a plurality of electrodes will be advanced through the tissue and to a desired position, as shown in FIG. 7A. Electrode positioning can include, for example, insertion and advancement through the skin and through the tissue of the patient. Electrode positioning and arrangement within the target tissue can be precisely controlled and may occur under the guidance of tissue imaging methodology (e.g., ultrasound imaging, X-ray, CT, etc.). FIG. 7B illustrates a cross-section view of a target tissue having a plurality of positioned needle electrodes.

In some embodiments, electrode positioning can be directed to smaller distances so as to further allow more precise control of the desired effect of the applied field on the tissue. Factors such as differential conductive properties and resistance or tissue impedance (e.g., differences in muscle, adipose, vasculature, etc.), as well as differential perfusion of blood through vascularized tissue, can limit the ability to control and/or predict effects of delivered current field traversing larger distances through tissue. In the present invention, distances between activated electrodes can be limited to shorter distances, such as a few centimeters or less, for improved control and predictability of current effects (e.g., tissue heating, field delivery, orientation, etc) on the targeted tissue. Thus, activated electrodes in a pair or group can be spaced less than about 4 cm apart. For example, adjacent electrodes of a pair or group will typically be positioned within about 0.1 cm to about 2 cm of each other. Distances of about 0.5 cm have been shown to be particularly effective in providing controlled and predictable field delivery, controlled tissue heating, as well as substantial therapeutic effect.

As described above, a plurality of electrodes can be positioned in the target tissue of a patient and the electrodes can be activated in pairs or groups to deliver the therapeutic current field to destroy cancerous tissue. A particular electrode of an array need not be confined to a single unit, but can be activated at different times in conjunction with different electrodes of the plurality. For example, differential activation can include activating a specific or selected series of electrode groups in a particular or predetermined order. In one embodiment, a series of selected pairs or groups can be activated in seriatim and/or in a predetermined order, with activation control typically being determined by operation or instructions (e.g., programming) of a control system or module. Sequences of group activations can be controlled and repeated, manually or by automation, as necessary to deliver an effective or desired amount of energy.

Such differential activation may advantageously allow delivery of fields throughout the target tissue and in a plurality of different directions. As shown above by way of example, a simple four electrode grouping of an array can be differentially activated in pairs, with each different pair of electrodes providing a different field delivery and orientation (possible field flow/orientations are illustrated by arrows). While activation of electrodes in discrete pairs provides simplicity, electrodes can be activated in groups for more diverse field orientation and deliver. For example, a delivery unit can include a centrally located electrode surrounded by spaced outer or secondary electrodes, with the applied field extending between the central electrode and the outer spaced electrodes. In this manner, the outer electrodes can essentially define an ablation volume with the inner/central electrode positioned within the volume. Field delivery in this way can be controlled and substantially contained within the ablation volume. Examples described herein illustrate electrode positioning including outer electrodes and an inner or centrally located electrode. Electrode positioning will not be limited to any particular configuration, and various arrangements will be possible.

Treatment time according to the present invention can be selected based on a variety of factors, such as characterization of the tissue, energy applications selected, patient characteristics, and the like. Energy application to a target tissue region during treatment according to the present invention can be selected from a few minutes to several hours. In some instances, effective treatment is expected to occur in about 5 minutes to 90 minutes. Effective preferential destruction of cancerous cells has been observed in less than one hour, and in many cases about 15-30 minutes of energy application. Treatment can include a single energy delivery period or dose, or multiple phases or doses of energy application. As described above, electrodes can be positioned in a first location and energy delivered, then moved to subsequent location(s) for subsequent energy delivery. Treatment can occur in phases or repeated, and/or may be coupled with additional or alternative treatments or energy delivery methods.

Figure 8:
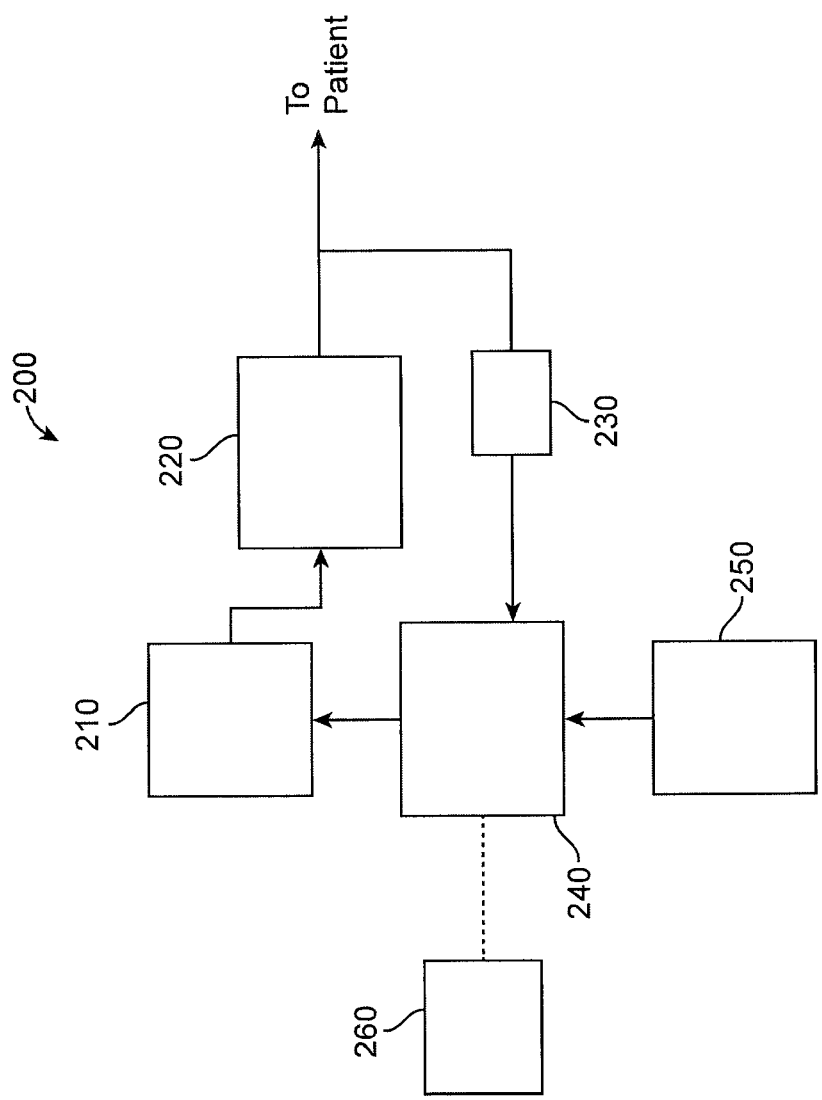
FIG. 8 includes a diagram illustrating a system according to an embodiment of the present invention.

A system according to an embodiment of the present invention is described with reference to FIG. 8. The system 200 can include incorporated therewith any device of the present invention for delivery of energy to the patient, and includes a power unit 210 that delivers energy to a driver unit 220 and than to electrode(s) of an inventive device. The components of the system individually or collectively, or in a combination of components, can comprise an energy source for a system of the invention. A power unit 210 can include any means of generating electrical power used for operating a device of the invention and applying electrical current to a target tissue as described herein. A power unit 210 can include, for example, one or more electrical generators, batteries (e.g., portable battery unit), and the like. One advantage of the systems of the present invention is the low power required for the ablation process. Thus, in one embodiment, a system of the invention can include a portable and/or battery operated device. A feedback unit 230 measures electric field delivery parameters and/or characteristics of the tissue of the target tissue region, measured parameters/characteristics including without limitation current, voltage, impedance, temperature, pH and the like. One or more sensors (e.g., temperature sensor, impedance sensor, thermocouple, etc.) can be included in the system and can be coupled with the device or system and/or separately positioned at or within the patient's tissue. These sensors and/or the feedback unit 230 can be used to monitor or control the delivery of energy to the tissue. The power unit 210 and/or other components of the system can be driven by a control unit 240, which may be coupled with a user interface 250 for input and/or control, for example, from a technician or physician. The control unit 240 and system 200 can be coupled with an imaging system 260 (see above) for locating and/or characterizing the target tissue region and/or location or positioning the device during use. The system can further optionally include a delivery unit or source of one or more immunostimulatory agents or adjuvants. Such a delivery unit or source can be wholly separate from other components of the system or may be incorporated with one or more other components. For example, a delivery unit or source may be coupled with or incorporated together with a probe or one or more electrodes of a probe (e.g., hollowed injection needle or electrode).

A control unit can include a, e.g., a computer or a wide variety of proprietary or commercially available computers or systems having one or more processing structures, a personal computer, and the like, with such systems often comprising data processing hardware and/or software configured to implement any one (or combination of) the method steps described herein. Any software will typically include machine readable code of programming instructions embodied in a tangible media such as a memory, a digital or optical recovering media, optical, electrical, or wireless telemetry signals, or the like, and one or more of these structures may also be used to transmit data and information between components of the system in any wide variety of distributed or centralized signal processing architectures.

Components of the system, including the controller, can be used to control the amount of power or electrical energy delivered to the target tissue. Energy may be delivered in a programmed or pre-determined amount or may begin as an initial setting with modifications to the electric field being made during the energy delivery and ablation process. In one embodiment, for example, the system can deliver energy in a "scanning mode", where electric field parameters, such as applied voltage and frequency, include delivery across a predetermined range. Feedback mechanisms can be used to monitor the electric field delivery in scanning mode and select from the delivery range parameters optimal for ablation of the tissue being targeted.

Systems and devices of the present invention can, though not necessarily, be used in conjunction with other systems, ablation systems, cancer treatment systems, such as drug delivery, local or systemic delivery, surgery, radiology or nuclear medicine systems, and the like. For example, as indicated above, systems and devices may include immunostimulatory agent or adjuvant delivery, and may be configured for delivery of such agents in various form (e.g., liquid, solid, suspensions, and the like). Another advantage of the present invention, is that treatment does not preclude follow-up treatment with other approaches, including conventional approaches such as surgery and radiation therapy. In some cases, treatment according to the present invention can occur in conjunction or combination with therapies such as chemotherapy. Similarly, devices can be modified to incorporate components and/or aspects of other systems, such as drug delivery systems, including drug delivery needles, electrodes, etc.

The following examples are intended to illustrate but not limit the invention.

EXAMPLES

Example 1

Initial testing included treatment of a breast cancer tumor model in Female Fisher-344 rats (Charles River). Rat breast cancer cells (MTLn-3) were initially grown in culture and subcutaneous tumors were produced by implanting cells from cultures into the abdomen of the animal. Tumors were grown to approximately 1 cm or greater in diameter followed by low-temperature or mild hyperthermia ablation treatment. As the MTLn-3 cell line is an aggressively proliferating cell line, tumors were highly metastatic and in some cases test animals presented more than one observable tumor. In animals presenting more than one tumor, one tumor was selected for direct insertion of electrodes for treatment with additional tumors left unaddressed by direct electrode insertion and energy application.

The probe used was of the triangle configuration with a central anode and three outer cathodes (e.g., similar to probe FIGS. 5A-5D). The radius of the probe from anode to cathode was three millimeters. The electrode probe was coupled to a System Control Module (SCM) designed to generate, deliver, monitor and control the therapeutic field within the specified treatment parameters. The SCM included of an integrated direct current (DC) battery power source, an alternating current (AC) inverter, a signal generator, a signal amplifier, an oscilloscope, an operator interface monitor, and a central processing unit (CPU). The SCM was battery powered and isolated from ground. AC current was derived from the integrated power inverter. An intermediate frequency (about 100 kHz) alternating current, sinusoidal wave form signal can be produced from the signal generator. Total power output is less than 1 watt. The treatment parameters are input by the operator.

Energy application treatment times included 30 minutes, 90 minutes, and about 3 hours. Effective treatment times of shorter duration, e.g., about 15 minutes, have been observed in separate studies. Significant tumor destruction relative to untreated control group animals was observed in a majority of the rats subject to treatment.

The energy application demonstrated a significant, direct tumor destructive effect on cancerous cells of the target treatment region. In addition to the direct effect of current application on cancerous cell viability, several observations suggested additional tumor cell destruction effects, possibly by an immune system mediated action including development of an in vivo immune memory and cancerous cell specific immune mediated effect. First, a subgroup of the treated animals surprisingly achieved long term survival and viability, suggesting a systemic remission of cancer treated. Because the tumor model was a highly metastatic cancerous cell line, it was expected that even if eradication of a locally treated tumor could be achieved, long term survival was unlikely as the highly metastatic cells would be expected to have spread to other regions of the animals body that were not directly subject to current application. Those metastatic cells would be expected to undergo proliferation and relatively rapidly produce lethal tumors, thereby limiting the possibility of long term survival absent some systemic response resulting from the localized treatment described above. Second, as noted above, while several animals in the treatment group exhibited multiple tumors, in each treated animal, only one tumor was selected for energy application during the testing. In several instances, untreated tumors that were remote from the treatment site appeared to exhibit reduced tumor volume several days following treatment.

Third, in one animal exhibiting multiple tumors, fluid removed from a first tumor subjected to current delivery was injected into a second tumor (not subjected to local current delivery), followed by observed volume reduction in the second tumor. Thus, a first tumor in the animal was selected for energy application as noted above. Following current delivery to the first tumor, a further step was performed where a hypodermic syringe was used to remove fluid from the first tumor treatment site. The removed fluid was then injected into a second tumor at a second tumor site remote from the first tumor, where the second tumor had not been directly subjected to local current delivery. A reduction in tumor volume at the second tumor following fluid injection was observed upon follow-up examination.

Fourth, several animals in the treatment group in which long term survival was achieved exhibited a reduced susceptibility to attempted tumor re-introduction and re-implantation following treatment. As noted above, rats of the treatment group were initially implanted (prior to energy application) with cancerous cells and tumors successfully grown. A subset of rats (n=2) of the treatment group subject to energy application as described exhibited no observable tumors following treatment, with that subset achieving surprisingly long term survival (e.g., greater than 12 months compared to about 3 weeks of expected survival). The two long-term surviving rats were later subject to cancerous cell implantation according to the same implantation protocol initially used. However, cancerous cell implantation following treatment was unsuccessful in implanting/growing subsequent tumors in those long term surviving animals, indicating a developed resistance to the cancerous cell line.

Fifth, histopathology analysis of tissue of treated animals has identified immune cells such as macrophages increasingly present about the target tissue following energy application, indicating a non-specific immune cell mediated response is at least initially elicited by the current application. In combination with other observations, e.g., including those listed above, initial localized macrophage infiltration and immune system mediated localized response to treatment suggests initial stages of development of a adaptive immune response in the host that is specific to the cancerous tissue treated and facilitated by the localized current application.

Example 2

Additional study will address an increased in vivo specific or adaptive immunological response of an individual subject against a cancerous cell species following current application treatment according to the present invention. In one example, a study will include several groups of animals for experimental groups and control. A control group (Group 1) can include tumor implantation (carcinoma tumors such as MTLn3 and MATB3 tumor cell lines in Fisher 344 rats, or 4T1 tumor cell line in BALB/c mice) into immunologically intact (normal) rats or mice and the time to death due to tumor metastasis measured with gross and microscopic pathological evaluation to document the metastatic sites and severity. Another group includes subjects where a primary or treatment site is ablated by low-heat energy application as described herein and the subjects are monitored for any reoccurrence of tumors (Group 2). Any subjects in Group 2 that survived past the time period where 80% of the mice in Group 1 died or demonstrated clinical signs of metastatic disease will be further evaluated for development of an immunological response that at least partially contributed to survival from metastatic spread of the cancer cells. These surviving subjects will be placed in Group 3, and the same tumor attempted for implantation into the subjects for evaluation of rate of acceptance of the transplanted tumor compared to implantation acceptance rate in the initial Group 2. A group of untreated subject animals with the same age as those in Group 3, which have no-prior tumor implantation or treatment, will also be transplanted with the tumor cells (Group 4). Group 4 can control for any decrease in the acceptance rate of tumor implantation is due to energy application/low-temperature ablation treatment induced immunity and not age dependant resistance to the tumor.

Pathological characterization of metastatic tumor sites and immunohistological characterization of immune cell (e.g., dendritic cells, macrophages, etc.) numbers and pattern in follicles of the tumors regional lymph nodes and the spleen can be used as an indirect assessment of immunological up-regulation of an immune response to the tumor following energy application therapy. Positive direct results of anti-tumor immunity in these studies would indicate that the current application according to the present invention not only destroyed the treated tumors directly, but also inhibited the growth of metastatic and untreated tumor foci within the animals through the induction of an antitumor immune response.

Example 3

Tumor destruction according to the present invention involves direct and indirect tumor kill, and potentially specific or adaptive antitumor immunologic effects. To provide evidence for the potential antitumor immunologic effects, low-heat or mild hyperthermia inducing current application to a target tissue as described herein is used to treat primary tumors and examine prevention of metastases in the tumor model. A tumor model selected will be an aggressive, spontaneously metastasizing tumor model, and may include those mirroring human breast cancer, prostate cancer, liver cancer, brain cancer, pancreatic cancer, or any variety of tumor models. When grown in an animal, highly metastatic tumors rapidly metastasize beyond the implantation site, e.g., to lung, liver, lymph nodes, brain, etc.

To confirm a specific or adaptive immune mediated tumor destruction by current application as described herein, tumors are grown in animals, followed by current application treatment and monitoring of survival. To determine whether the therapy could enhance antitumor immunity and reduce metastatic growth, the lymph node (LN) cells from treated and control animals are transferred to naive recipient animals. Recipients are challenged with a tumorigenic dose of the same tumor cells after adoptive transfer and primary and secondary tumor growth in the recipients was examined.

Animals receiving LN cells from treated animals are examined for significant increased survival when compared to animals receiving LN cells from control animals. LN cells isolated from treated animals, but not control animals, are examined for significantly inhibited primary tumor growth in recipients and reduction in the number of metastases present after tumor challenge. Depletion of certain immune cells, such as $CD8^+$ T cells, from the LN can be examined for an abolished effect. Results will indicate whether current application therapy as described herein not only destroys the treated tumors directly but also controls growth of untreated tumors through induction of a specific host antitumor immune response.

Example 4

In another example, evidence for specific/adaptive immunologic effects resulting from delivery of current application to a target tissue as described herein may optionally further include examination of immuno-compromised animal model(s). For example, a study may include two groups of animals as experimental and control groups. A control group (Group 1) can include tumor implantation (such as 3T3 mouse epithelial tumor cells, CT26 mouse colorectal tumor cells, or EMT6/AR1 mouse breast cancer cells) into wild-type (genomically normal) C57Bl/6 mice and the time to death due to tumor metastasis measured with gross and microscopic pathological evaluation to document the metastatic sites and severity. Tumors can be implanted into a second group of C57Bl/6 mice having a genetic deficiency in RAG1 or RAG2 genes (Group 2). Mice lacking RAG1 or RAG2 completely lack natural killer T, T and B cells. However, DNA repair mechanisms are intact in nonlymphoid tissues. The implanted tumors in both groups of mice can be ablated by low-heat energy application as described herein and the animals monitored for any reoccurrence of tumors.

Comparison of clinical and pathological characterization of the primary tumor and metastatic tumor sites between the two groups can provide direct evidence regarding the role of underlying immunocompetence in suppressing tumor growth and development, and impact on animal well-being. Immunohistological characterization of tumor-infiltrating immune cells can provide additional information regarding immune-mediated anti-tumor immunity. Positive direct results of anti-tumor immunity, delayed tumor growth or metastases, and improved survival in control animals compared to RAG-deficient mice would indicate that the current application according to the present invention not only destroyed the treated tumors directly, but also inhibited the growth of metastatic and untreated tumor foci within the animals through the induction of an antitumor immune response.

Example 5

In another example, study may optionally further include examination of immunosuppressed (non-genetically) animal model(s). A study may include three groups of animals as control and experimental treatment groups. Tumor cells (such as 3T3 mouse epithelial tumor cells, CT26 mouse colorectal tumor cells, or EMT6/AR1 mouse breast cancer cells) can be implanted into each groups of wild-type C57Bl/6 mice. The implanted tumors in each group of mice can be ablated by low-heat energy application as described herein and the animals monitored for any reoccurrence of tumors. After tumor ablation, animals in the experimental treatment group (Group 1) can receive a cocktail of antibodies to deplete CD4 and CD8 T cells and IFN-γ. Animals in a separate experimental treatment group (Group 2) can receive adjuvant (such as Freund's incomplete adjuvant) after tumor ablation to non-specifically stimulate an immune response. The response in experimental Group 1 and 2 animals and untreated control animals (Group 3) can be followed to evaluate time to death due to tumor metastasis measured with gross and microscopic pathological evaluation to document the metastatic sites and severity.

Comparison of clinical and pathological characterization of the primary tumor and metastatic tumor sites between the experimental treatment groups compared to controls can provide direct evidence regarding the role of suppressed immunity (Group 1 vs Group 3) or stimulated immunity (Group 2 vs Group 3) in altering tumor growth and development, and the associated impact on animal well-being. Immunohistological characterization of tumor-infiltrating immune cells can provide additional information regarding immune-mediated anti-tumor immunity. Positive direct results of anti-tumor immunity, delayed tumor growth or metastases, and improved survival among immunostimulated animals (or reduced performance in immunosuppressed animals) in these studies would indicate that the current application according to the present invention not only destroyed the treated tumors directly, but also inhibited the growth of metastatic and untreated tumor foci within the animals through the induction of an antitumor immune response.

Example 6

Additional study will involve in vitro analysis of an increased immunological response of an individual subject against a cancerous cell species following current application treatment according to the present invention. In one example, a study will determine whether RF treatment of experimental VX-2T tumors in rabbit skeletal muscle stimulates immune responses to VX-2T tumor cells. Activation of a cellular immune response (lymphoproliferation) will be determined by quantifying T-cell proliferation to VX-2T cells before and after RF treatment in a Lymphoproliferation Assay (LPA). Activation of a humoral immune response (antibody production) will be determined by detection of specific antibodies to VX-2T in an Enzyme-Linked Immunosorbent Assay (ELISA). The Experimental design will involve isolation of PBMCs (peripheral blood mononuclear cells or mixed lymphocytes) and serum from rabbit blood prior to RF treatment and at two to four weeks after treatment.

Figure 9:
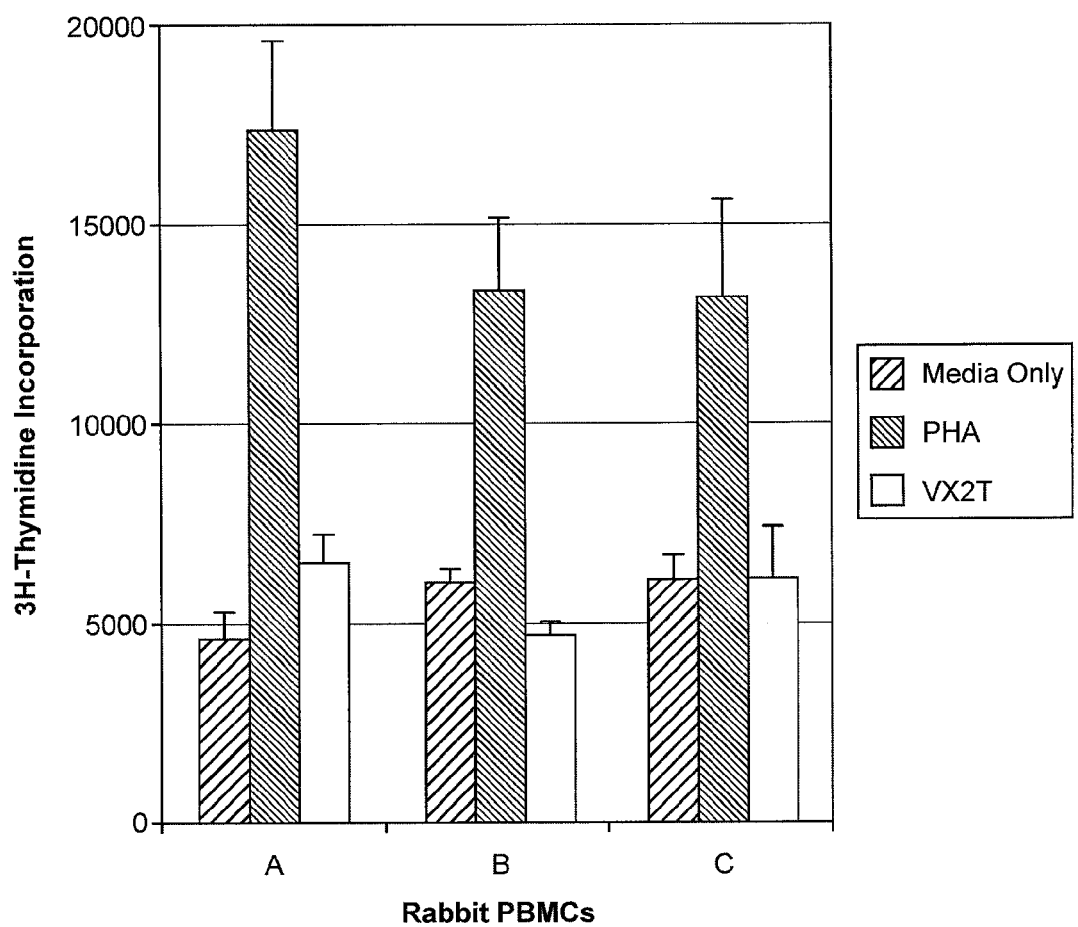
FIG. 9 shows lymphocyte proliferation data.

The LPA is the classic method for assessing lymphocyte response to stimulation. Lymphocytes proliferate after incubation in tissue-culture microtiter plates with non-specific mitogens such as phytohemaglutin A (PHA) or with a specific antigen such as VX-2T cell lysates. Proliferation can be measured by a number of ways. For example, proliferation is measured by $^3$H-thymidine incorporation. The degree of 3H-thymidine incorporation provides an indication of general lymphocyte activation to a specific antigen. Activation is often expressed as the stimulation index: SI=($^3$H-thy incorporation in media containing antigen)÷($^3$H-thy incorporation in media alone). FIG. 9 shows an example of 3 naïve rabbit PBMC response to PHA and to VX-2T cell lysate. The SI to PHA for samples A-C is 3.9, 2.2 and 2.2 respectively. SI of 1.0 or lower indicates no response to VX2T. Increase of the SI to VX-2T following RF treatment will be examined.

The ELISA is a biochemical technique used in immunology to detect the presence of an antibody or an antigen. In this case, the analysis will look for antibodies to VX-2T that are generated by rabbits following RF treatment. VX-2T cell lysate (the antigen) is immobilized on a solid surface such as a 96-well plastic microtiter plate. Then samples of diluted rabbit serum obtained before and after RF treatment are added. Following this, an indicator antibody (secondary antibody) with an attached enzyme such as goat anti-rabbit conjugated to horse-radish peroxidase is added. Thorough washing of wells is done following each incubation step to remove non-specifically bound proteins. Detection of anti-VX-2T antibodies generated in rabbits will be seen after addition of substrate for the enzyme-linked secondary antibody as a visible color change that can be measured by light absorption. It is expected that antibodies may be detected after tumor implantation as often is the case to any foreign proteins but will increase significantly after RF treatment. These antibodies may play an ancillary role in tumor clearance.

It is understood that the examples and embodiments described herein are for illustrative purposes only and that various modifications or changes in light thereof will be suggested to persons skilled in the art and are to be included within the spirit and purview of this application and scope of the appended claims. Numerous different combinations, including combinations of embodiments described herein, are possible, and such combinations are considered part of the present invention.

What is claimed is:

1. A method for delivering electric fields to a target tissue of a patient for destruction of cancerous cells, comprising:
    identifying a first target tissue site having cancer cells to destroy with remote electrical current flow treatment at an identified second target tissue site, the first identified target tissue site remote from the second identified target tissue site; and
    based on the step of identifying the first target tissue site, establishing an electrical current flow through an electrical treatment volume of the target tissue at the second identified target tissue site so as to preferentially destroy cancerous cells located in the electrical treatment volume and wherein the electrical current flow at the second identified target tissue site induces a specific anti-cancerous cell immune response in the patient to treat the first identified target tissue site.

2. The method of claim 1, wherein the electrical current flow is selected such that thermal based protein coagulation and denaturation in the cancerous cells or tissue is substantially avoided.

3. The method of claim 1, wherein the second target tissue is heated to less than about 50 degrees C. during a phase of treatment.

4. The method of claim 1, wherein the electrical current flow provides a voltage field less than about 50 V/cm.

5. The method of claim 1, wherein the electrical current flow comprises a frequency between about 50 kHz and about 300 kHz.

6. A method for delivering electric fields to a target tissue of a patient for destruction of cancerous cells, comprising:
identifying a first target tissue site having cancer cells to destroy with remote electrical current flow treatment at a second identified target tissue site, the first identified target tissue site remote from the second identified target tissue site; and
based on the step of identifying the first target tissue site, eliciting destruction of cancerous cells of the first identified target tissue site by establishing an electrical current flow through a volume of the second identified target tissue site so as to preferentially destroy cancerous cells in the electrical treatment volume;
wherein a specific host anti-cancerous cell immune response is induced at the second identified target tissue site so as to control growth of cancerous cells at the first identified target tissue site that has not directly received electrical current flow.

7. The method of claim 6, wherein cancerous cells have been seeded at the second target tissue site.

8. The method of claim 6, wherein the electrical current flow is selected such that thermal based protein coagulation and denaturation in the cancerous cells or tissue is substantially avoided.

9. The method of claim 6, wherein the second target tissue is heated to less than about 50 degrees C.

10. The method of claim 6, wherein the electrical current flow provides a voltage field less than about 50 V/cm.

11. The method of claim 6, wherein the electrical current flow comprises a frequency between about 50 kHz and about 300 kHz.

12. A method for delivering electric fields to a target tissue of a patient for destruction of cancerous cells, comprising:
identifying a first target tissue site having cancer cells to destroy with remote electrical current flow treatment at an identified second target tissue site, the first identified target tissue site remote from the second identified target tissue site;
based on the step of identifying the first target tissue site, establishing an electrical current flow through an electrical treatment volume of the target tissue at the second identified target tissue site so as to preferentially destroy cancerous cells located in the electrical treatment volume and wherein the electrical current flow at the second identified target tissue site induces a specific anti-cancerous cell immune response in the patient to treat the first identified target tissue site; and
administering an immunostimulatory agent or adjuvant to the patient.

13. The method of claim 12, wherein the administering an immunostimulatory agent or adjuvant to the patient comprises a systemic administration.

14. The method of claim 12, wherein the administering an immunostimulatory agent or adjuvant to the patient comprises a local administration.

15. A method for delivering electric fields to a target tissue of a patient for destruction of cancerous cells, comprising:
identifying a first target tissue site having cancer cells to destroy with remote electrical current flow treatment at a second identified target tissue site, the first identified target tissue site remote from the second identified target tissue site;
based on the step of identifying the first target tissue site, eliciting destruction of cancerous cells of the first identified target tissue site by establishing an electrical current flow through a volume of the second identified target tissue site so as to preferentially destroy cancerous cells in the electrical treatment volume;
wherein a specific host anti-cancerous cell immune response is induced at the second identified target tissue site so as to control growth of cancerous cells at the first identified target tissue site that has not directly received electrical current flow; and
administering an immunostimulatory agent or adjuvant to the patient.

16. The method of claim 15, wherein the administering an immunostimulatory agent or adjuvant to the patient comprises a systemic administration.

17. The method of claim 15, wherein the administering an immunostimulatory agent or adjuvant to the patient comprises a local administration.

* * * * *